United States Patent [19]

Narimatsu et al.

[11] Patent Number: 5,762,610
[45] Date of Patent: Jun. 9, 1998

[54] PRESSURE PULSE WAVE DETECTING APPARATUS

[75] Inventors: Kiyoyuki Narimatsu, Kasugai; Hideo Nishibayashi, Inuyama, both of Japan

[73] Assignee: Colin Corporation, Komaki, Japan

[21] Appl. No.: 675,675

[22] Filed: Jul. 3, 1996

[51] Int. Cl.$^6$ .............................. A61B 5/021; A61B 5/02
[52] U.S. Cl. .......................... 600/500; 600/502; 600/503; 600/504; 600/527
[58] Field of Search ..................................... 128/687, 689, 128/690, 691, 714; 600/500, 502, 503, 504, 527

[56] References Cited

U.S. PATENT DOCUMENTS

| | | | |
|---|---|---|---|
| 4,830,017 | 5/1989 | Perry et al. | 128/687 |
| 5,176,143 | 1/1993 | Eckerle et al. | 128/677 |
| 5,238,000 | 8/1993 | Niwa | 128/689 |
| 5,240,007 | 8/1993 | Pytel et al. | |
| 5,261,414 | 11/1993 | Aung et al. | 128/690 |
| 5,279,303 | 1/1994 | Kawamura et al. | 128/683 |

FOREIGN PATENT DOCUMENTS

| | | |
|---|---|---|
| 1155827 | 6/1989 | Japan. |
| 1-126205 | 8/1989 | Japan. |
| 2-177937 | 7/1990 | Japan. |

*Primary Examiner*—William E. Kamm
*Assistant Examiner*—Carl H. Layno
*Attorney, Agent, or Firm*—Oliff & Berridge, PLC

[57] ABSTRACT

An apparatus for detecting a pressure pulse wave from a living subject, including a pressure pulse wave sensor which detects a pressure pulse wave which is produced from an artery of the subject, a pressing device which presses the sensor against the artery via a body surface of the subject, a position changing device which moves the sensor and thereby changes a position of the sensor relative to the artery in a direction of width of the artery, and a control device which determines, based on the pulse wave detected by the sensor, an optimum pressing position of the sensor where the sensor is pressed against the artery by the pressing device, and controls the position changing device to position the sensor at the optimum pressing position, the control device functioning as a moving device for controlling the position changing device to move the sensor relative to the artery while the sensor is pressed on the body surface by the pressing device, a determining device for determining the optimum pressing position of the sensor based on the pressure pulse wave detected by the sensor while the sensor is pressed by the pressing device and is moved by the position changing device under control of the moving device, and a stopping device for controlling the position changing device to stop moving the sensor when the optimum pressing position of the sensor is determined by the determining device.

11 Claims, 8 Drawing Sheets

PRESSURE PULSE WAVE DETECTING APPARATUS

BACKGROUND OF THE INVENTION

1. Field of the Invention

The present invention relates to a pressure pulse wave detecting apparatus including a pressure pulse wave sensor which is adapted to be pressed against a superficial artery of a living subject via body surface or skin of the subject to detect a pressure pulse wave which is propagated in the artery.

2. Related Art Statement

There is known a pressure pulse wave (PPW) detecting apparatus which includes a pressure pulse wave (PPW) sensor for detecting a pressure pulse wave (PPW) which is produced from an artery of a living subject, a pressing device for pressing the sensor against the artery via a body surface of the subject, and a position changing device for moving the sensor and thereby changing a position of the sensor relative to the artery in a direction of width of the artery. The PPW detecting apparatus detects the PPW through the PPW sensor which is located at an optimum pressing position by the position changing device and is pressed with an optimum pressing force by the pressing device. This PPW detecting apparatus is disclosed in, e.g., Japanese Utility Model Application laid open for inspection purposes under Publication No. 2(1990)-126205.

The above PPW detecting apparatus further includes a control device which controls, when a predetermined position-changing-operation starting condition is satisfied, the position changing device to move the PPW sensor by a predetermined distance while the sensor is not pressed by the pressing device, determines an optimum pressing position of the sensor where the sensor is most advantageously pressed by the pressing device, based on the PPW detected by the sensor which is pressed at the moved position by the pressing device, and controls the position changing device to position the sensor at the determined optimum pressing position. In addition, the PPW detecting device includes an optimum-pressing-force determining means for determining an optimum pressing force which is applied to the sensor by the pressing device, based on the PPW detected by the PPW sensor located at the optimum pressing position while the pressing force applied to the sensor is continuously changed by the pressing device. Thus, the PPW detecting apparatus detects the PPW through the PPW sensor which is located at the optimum pressing position right above the artery of the subject and is pressed with the optimum pressing force.

However, when the pressing force applied to the PPW sensor located at the optimum pressing position is continuously increased for determining an optimum pressing force applied to the sensor, a portion of the artery right below the body surface pressed by a press surface of the sensor may be moved away from below the press surface, since that portion of the artery is tensed between adjacent portions of the same because of the elasticity thereof. In the latter case, it is needed once more to increase, after the optimum pressing position is determined, the pressing force applied to the sensor, for determining the optimum pressing force. Thus, the prior PPW detecting apparatus cannot quickly determine an optimum pressing force of the PPW sensor, i.e., optimum pressing force applied to the PPW sensor by the pressing device and accordingly may suffer from a long interruption period in which the PPW sensor cannot detect the PPW from the subject.

SUMMARY OF THE INVENTION

It is therefore an object of the present invention to provide a pressure pulse wave detecting apparatus which includes a pressure pulse wave sensor and quickly determines an optimum pressing position of the sensor relative to an artery of a living subject.

The above object has been achieved according to the present invention, which provides an apparatus for detecting a pressure pulse wave from a living subject, comprising a pressure pulse wave sensor which detects a pressure pulse wave which is produced from an artery of the subject, a pressing device which presses the sensor against the artery via a body surface of the subject, a position changing device which moves the sensor and thereby changes a position of the sensor relative to the artery in a direction of width of the artery, and a control device which determines, based on the pressure pulse wave detected by the sensor, an optimum pressing position of the sensor relative to the artery where the sensor is pressed against the artery by the pressing device, and controls the position changing device to position the sensor at the optimum pressing position, the control device comprising moving means for controlling the position changing device to move the sensor relative to the artery while the sensor is pressed on the body surface by the pressing device, optimum pressing-position determining means for determining the optimum pressing position of the sensor based on the pressure pulse wave detected by the sensor while the sensor is pressed by the pressing device and is moved by the position changing device under control of the moving means, and stopping means for controlling the position changing device to stop moving the sensor when the optimum pressing position of the sensor is determined by the optimum-pressing-position determining means.

In the pressure pulse wave detecting apparatus constructed as described above, the optimum-pressing-position determining means determines the optimum pressing position of the sensor based on the pressure pulse wave detected by the sensor while the sensor is pressed by the pressing device and is moved by the position changing device under control of the moving means, and the stopping means controls the position changing device to stop moving the sensor when the optimum pressing position of the sensor is determined by the optimum-pressing-position determining means. Since the optimum pressing position of the sensor is determined while the sensor is pressed and moved and the sensor is stopped at the optimum pressing position while being pressed, the artery does not move away from below the press surface of the sensor, when the pressing force applied to the sensor is continuously increased from the state in which the sensor is stopped and pressed, for determining the optimum pressing force applied to the sensor. Thus, the optimum pressing force can be determined with rapidity and reliability. That is, the present apparatus does not need any more to increase, after the optimum pressing position is determined, the pressing force applied to the sensor, for determining the optimum pressing force. Thus, the present apparatus can quickly determine an optimum pressing force of the PPW sensor and accordingly shorten an interruption period in which the sensor cannot detect the PPW from the subject. That is, the period in which the pressing force of the sensor is continuously changed for determining the optimum pressing force is minimized and simultaneously the interruption period in which the sensor cannot detect the PPW is minimized.

According to a preferred feature of the present invention, the pressure pulse wave sensor comprises a plurality of pressure-sensing elements and a press surface in which an array of the pressure sensing elements extends in a direction in which the sensor is moved by the position changing device, the press surface being adapted to be pressed against the artery via the body surface so that each of the pressure-sensing elements detects a pressure pulse wave produced from the artery.

According to another feature of the present invention, the optimum-pressing-position determining means comprises means for judging whether a pulse amplitude of a pressure pulse wave detected by at least one first sensing element belonging to one of opposite end ranges of the array of pressure-sensing elements is substantially equal to a pulse amplitude of a pressure pulse wave detected by at least one second sensing element belonging to the other end range of the array of pressure-sensing elements, and determining, as the optimum pressing position of the sensor, a current position of the sensor when a positive judgment is made. In this case, the sensor is stopped at the optimum pressing position with higher accuracy than the case where the sensor is stopped when it is identified that one sensing element belonging to a middle range of the array of pressure-sensing elements between the opposite end ranges thereof detects a pressure pulse wave (PPW) having the greatest pulse amplitude of the respective pulse amplitudes of the PPWs detected by all the sensing elements.

According to another feature of the present invention, the apparatus further comprises optimum-sensing-element selecting means for selecting, as an optimum sensing element, at least one third sensing element belonging to a middle range of the array of pressure-sensing elements of the pressure pulse wave sensor stopped at the optimum pressing position, the middle range being located between the opposite end ranges.

According to another feature of the present invention, the apparatus further comprises a blood pressure measuring device which measures a standard blood pressure value of the subject.

According to another feature of the present invention, the blood pressure measuring device comprises an inflatable cuff which is adapted to be wound around a body portion of the subject, a supplying device which supplies the cuff with a pressurized fluid to increase a fluid pressure in the cuff and thereby inflate the cuff, a fluid-pressure sensor which detects the pressure of the cuff, and standard-blood-pressure determining means for determining the standard blood pressure value of the subject based on variation of pulse amplitudes of a pulse wave which is produced in the cuff and detected by the fluid-pressure sensor.

According to another feature of the present invention, the apparatus further comprises relationship determining means for determining a relationship between blood pressure and pressure pulse wave magnitude, based on the standard blood pressure value measured by the blood pressure measuring device and a magnitude of the pressure pulse wave detected by the optimum sensing element of the pressure pulse wave sensor stopped at the optimum pressing position.

According to another feature of the present invention, the apparatus further comprises monitor-blood pressure determining means for determining, according to the relationship determined by the relationship determining means, a monitor blood pressure value of the subject based on a magnitude of each of heartbeat-synchronous pulses of the pressure pulse wave detected by the optimum sensing element of the pressure pulse wave sensor stopped at the optimum pressing position.

According to another feature of the present invention, the apparatus further comprises a display device which displays at least one of the standard blood pressure value measured by the blood pressure measuring device, the monitor blood pressure value determined by the monitor-blood-pressure determining means, and a waveform of the pressure pulse wave detected by the optimum sensing element of the pressure pulse wave sensor stopped at the optimum pressing position.

According to another feature of the present invention, the pressing device comprises an elastic diaphragm to which the pressure pulse wave sensor is fixed, a housing to which the diaphragm is fixed to cooperate with the housing to define a pressure chamber, and a supplying device which supplies the pressure chamber with a pressurized fluid to increase a fluid pressure in the pressure chamber, inflate the diaphragm, and thereby press the sensor on the body surface of the subject.

According to another feature of the present invention, the position changing device comprises an internally threaded nut which is fixed to the housing, an externally threaded screw which is threadedly engaged with the nut, and a drive device which rotates the screw and thereby moves the pressure pulse wave sensor relative to the artery of the subject.

According to another feature of the present invention, the pressing device comprises means for pressing the pressure pulse wave sensor with a predetermined pressing force on the body surface of the subject.

According to another feature of the present invention, the apparatus further comprises optimum-pressing-force determining means for determining an optimum pressing force of the pressing device applied to the artery of the subject via the body surface, based on the pressure pulse wave detected by the pressure pulse wave sensor stopped at the optimum pressing position while the pressing force of the pressing device is increased from the predetermined pressing force.

BRIEF DESCRIPTION OF THE DRAWINGS

The above and optional objects, features, and advantages of the present invention will better be understood by reading the following detailed description of the preferred embodiments of the invention when considered in conjunction with the accompanying drawings, in which.

DETAILED DESCRIPTION OF THE PREFERRED EMBODIMENTS

Referring to FIGS. 1 to 8, there will be described a continuous blood pressure (BP) monitor including a pressure pulse wave (PPW) detecting apparatus embodying the present invention. The continuous BP monitor may be used to monitor BP values of a patient who is undergoing, or has undergone, a surgical operation.

Figure 1:
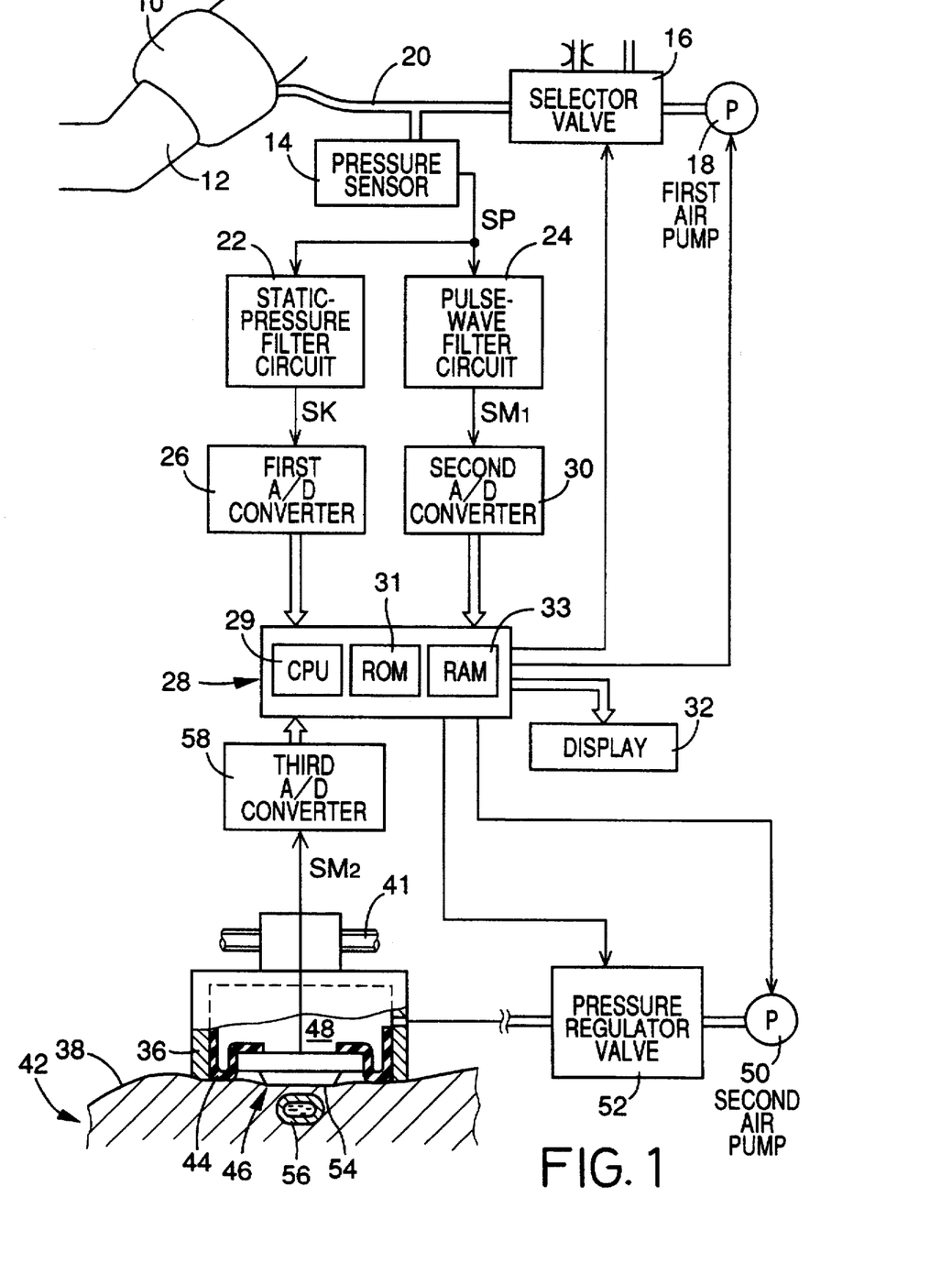
FIG. 1 is a diagrammatic view of a continuous blood pressure (BP) monitor including a pressure pulse wave (PPW) detecting probe to which the present invention is applied.

In FIG. 1, reference numeral 10 designates an inflatable cuff including a rubber bag and a band-like cloth bag in which the rubber bag is accommodated. The cuff 10 is wound around, e.g., an upper arm 12 of a patient. The cuff 10 is connected via piping 20 to a pressure sensor 14, a selector valve 16, and a first air pump 18. The selector valve 16 is selectively placed, under control of a control device 28, in a first state in which the valve 16 permits pressurized air to be supplied from the air pump 18 to the cuff 10 to increase the pressure of the cuff 10 (hereinafter, referred to as the "cuff pressure"), a second state in which the valve 16 causes the cuff 10 to be deflated slowly, and a third state in which the valve 16 causes the cuff 10 to be deflated quickly.

The pressure sensor 14 detects the cuff pressure (i.e., the pressure of the cuff 10), and generates a pressure signal, SP, representing the detected cuff pressure. The pressure signal SP is supplied to each of a static-pressure filter circuit 22 and a pulse-wave filter circuit 24. The static-pressure filter circuit 22 includes a low-pass filter which extracts, from the pressure signal SP, a cuff-pressure signal, SK, representing a static or direct-current component of the pressure signal SP. The cuff-pressure signal SK is supplied via a first analog-to-digital (A/D) converter 26 to the control device 28. The pulse-wave filter circuit 24 includes a band-pass filter which extracts, from the pressure signal SP, a pulse-wave signal, $SM_1$, representing an oscillating or alternating-current component of the pressure signal SP. The pulse-wave signal $SM_1$ is supplied via a second A/D converter 30 to the control device 28. The oscillating or alternating-current component represented by the pulse-wave signal $SM_1$ corresponds to an oscillatory pressure wave, i.e., pulse wave which is produced from a brachial artery (not shown) of the patient in synchronism with the heartbeat of the patient and is propagated via skin tissue to the cuff 10. In the present embodiment, this pulse wave is referred to as the "cuff pulse wave" to be distinguished from a "pressure pulse wave" which will be described later. Thus, the pulse-wave filter circuit 24 functions as a cuff pulse wave sensor.

The control device 28 is provided by a microcomputer including a central processing unit (CPU) 29, a read only memory (ROM) 31, a random access memory (RAM) 33, and an input and output (I/O) port (not shown). The CPU 29 processes input signals, including the signals SK, $SM_1$, by utilizing the temporary-storage function of the RAM 33, according to control programs pre-stored in the ROM 31. In addition, the CPU 29 supplies drive signals via the I/O port to drive circuits (not shown) which are provided for the selector valve 16 and the air pump 18, respectively. Thus, the CPU 29 controls the valve 16 and the pump 18. For example, when an oscillometric BP measurement using the cuff 10 is carried out to calibrate the present BP monitor, the CPU 29 controls the valve 16 and the pump 18 to increase quickly the cuff pressure up to a predetermined target value and subsequently decrease the cuff pressure at a low rate of 2 to 3 mmHg/sec. Based on the variation of the pulse wave represented by the pulse-wave signal $SM_1$ produced by the pulse-wave filter circuit 24 during the low-rate decreasing of the cuff pressure, the CPU 29 determines a systolic and a diastolic BP value of the patient, according to the known oscillometric BP measuring method. In addition, the CPU 29 controls a display 32 to display the thus determined BP values.

Figure 2:
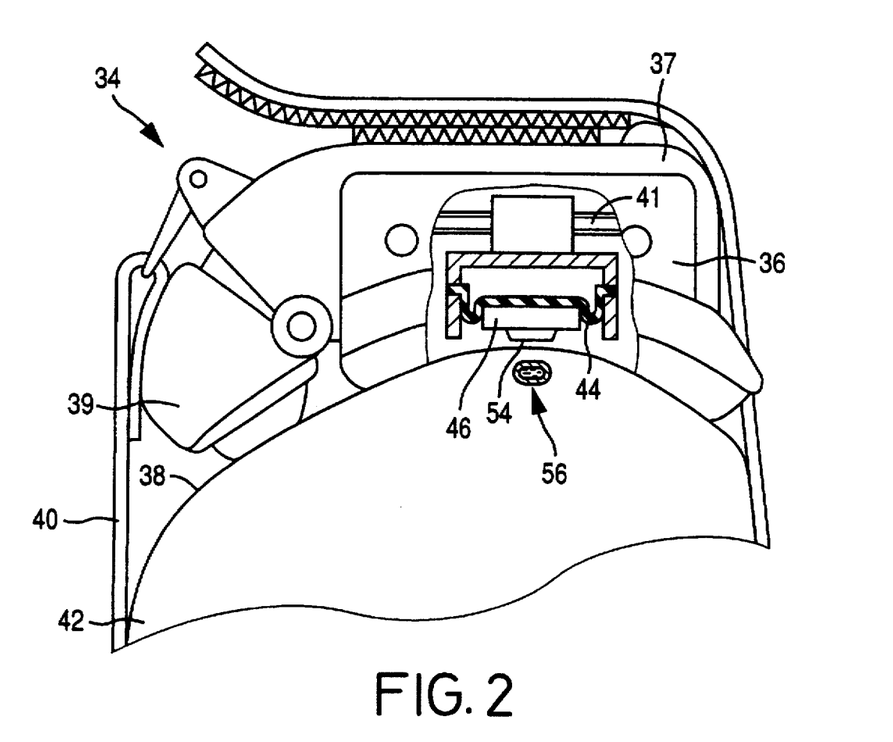
FIG. 2 is an enlarged view of a part of the PPW detecting probe of FIG. 1.

As shown in FIG. 2, a pressure-pulse-wave (PPW) detecting probe 34 includes a casing 37, a container-like sensor housing 36 accommodated in the casing 37, and a feed screw 41 which is threadedly engaged with a nut fixed to the sensor housing 36 and is rotated by an electric motor (not shown) to feed the housing 36 in a direction of width of a radial artery 56, i.e., in a direction intersecting the artery 56. The electric motor is accommodated in a drive section 39. A fastening band 40 is connected to the casing 37. With the help of the fastening band 40, the PPW detecting probe 34 is detachably attached to a wrist 42 of the patient such that an opening of the container-like sensor housing 36 is opposed to a body surface 38 of the patient. A PPW sensor 46 is secured via an elastic diaphragm 44 to inner surfaces of the sensor housing 36 such that the PPW sensor 46 is movable relative to the housing 36 and is advanceable through the opening of the housing 36 toward the body surface 38 of the patient. The sensor housing 36 and the diaphragm 44 cooperate with each other to define a pressure chamber 48, which is supplied with pressurized air from a second air pump 50 via a pressure regulator valve 52. Thus, the PPW sensor 46 is pressed on the body surface 38 with a pressing force corresponding to the pressure of the pressure chamber 48. In the present embodiment, the pressing forces of the PPW sensor 46 applied to the body surface 38 or the radial artery 56 are indicated in terms of the pressure values (mmHg) of the pressure chamber 48.

The sensor housing 36, the diaphragm 44, the pressure chamber 48, the second air pump 50, the pressure regulator valve 52, etc. cooperate with one another to provide a pressing device 62 (FIG. 5) which presses the PPW sensor 46 against the radial artery 56 via the body surface or skin tissue 38. The feed screw 41, the sensor housing 36, the diaphragm 44, the electric motor (not shown), etc. cooperate with one another to provide a position changing device 64 (FIG. 5) which moves the PPW sensor 46 and thereby changes a position of the PPW sensor 46 relative to the radial artery 56 in the direction of width of the artery 56.

Figure 3:
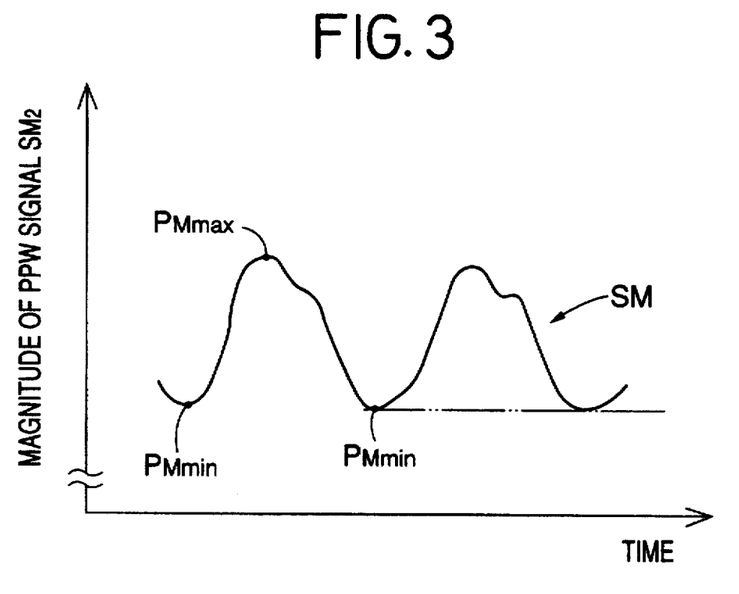
FIG. 3 is a graph showing a pressure pulse wave (PPW) detected by each of a plurality of pressure-sensing elements of a pressure pulse wave (PPW) sensor of the PPW detecting probe of FIG. 1.

The PPW sensor 46 includes a semiconductor chip formed of a monocrystalline silicon which has a press surface 54, and a number of pressure-sensing semiconductor elements (not shown) which are arranged, in the press surface 54, in an array at a regular interval of distance (about 0.2 mm), such that the array of pressure-sensing elements extends in the direction of width of the radial artery 56, i.e., in a direction of movement of the PPW sensor 46 parallel to the feed screw 41. When the PPW sensor 46 is pressed against the radial artery 56 via the body surface 38 of the wrist 42, the PPW sensor 46 detects an oscillatory pressure wave, i.e., pressure pulse wave (PPW) which is produced from the radial artery 56 in synchronism with the heartbeat of the patient and is propagated via the body surface 38 to the sensor 46. The PPW sensor 46 generates a PPW signal, $SM_2$, representing the detected PPW, and supplies the PPW signal $SM_2$ to the control device 28 via a third A/D converter 58. FIG. 3 shows an example of the magnitudes of PPW signal $SM_2$ generated by the PPW sensor 46.

The CPU 29 of the control device 28 processes the input signals, including the PPW signal $SM_2$, by utilizing the temporary-storage function of the RAM 33, according to the control programs pre-stored in the ROM 31, and supplies drive signals to drive circuits (not shown) which are provided for the second air pump 50 and the pressure regulator valve 52, respectively. Thus, the CPU 29 controls the pump 50 and the valve 52 and thereby regulates the pressure of the pressure chamber 48.

When a continuous BP monitoring operation is carried out, the CPU 29 determines an optimum pressing force, $P_{HDPO}$, of the PPW sensor 46 applied to the radial artery 56, based on the PPW obtained while the pressure of the pressure chamber 48 is slowly changed, and controls the pressure regulator valve 52 to maintain the pressure of the chamber 48 at the determined optimum pressing force $P_{HDPO}$. In addition, the CPU 29 determines a relationship between BP values and PPW magnitudes $P_M$ (i.e., absolute voltage values of the PPW signal $SM_2$), based on systolic and diastolic BP values, $BP_{SYS}$, $BP_{DIA}$, measured using the cuff 10 according the oscillometric BP measuring method, and a maximum and a minimum magnitude, $P_{Mmax}$, $P_{Mmin}$, of one heartbeat-synchronous pulse of the PPW detected by the PPW sensor 46 being pressed on the body surface 38 with the optimum pressing force $P_{HDPO}$. According to the thus determined relationship, the CPU 29 determines a systolic and a diastolic BP value (i.e., monitor BP values), $MBP_{SYS}$, $MBP_{DIA}$, of the patient, based on a maximum magnitude (i.e., upper-peak magnitude) $P_{Mmax}$ and a minimum magnitude (i.e., lower-peak magnitude), $P_{Mmin}$, of each of successive heartbeat- synchronous pulses of the PPW detected by the PPW sensor 46 being pressed on the body surface 38 with the optimum pressing force $P_{HDPO}$. Subsequently, the CPU 29 controls the display 32 to successively display, for each heartbeat-synchronous pulse, the thus determined monitor BP values $MBP_{SYS}$, $MBP_{DIA}$, in digits, and continuously display the waveform of the PPW detected by the PPW sensor 46. This waveform represents the instantaneous monitor BP values MBP of the patient.

Figure 4:
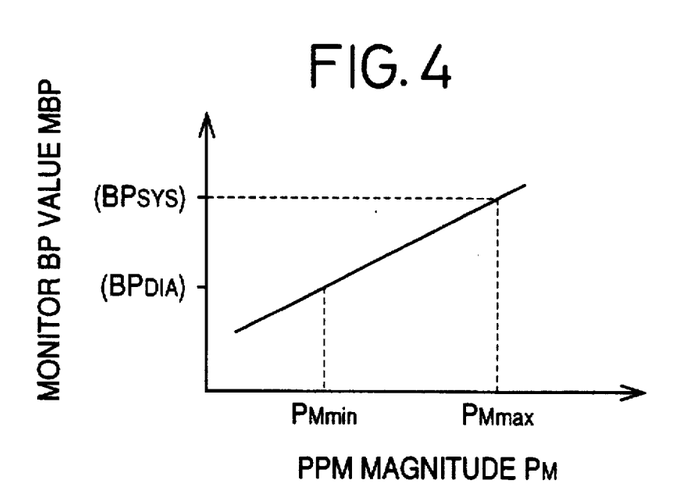
FIG. 4 is a graph showing a relationship determined by the BP monitor of FIG. 1.

FIG. 4 shows an example of a relationship between BP values (monitor BP values MBP) and PPW magnitudes $P_M$ that is determined by the CPU 29. This relationship is expressed by the following linear function (1):

$$MBP = A \cdot P_M + B \qquad (1)$$

where A is a constant corresponding to the slope of the linear function (1) and B is a constant corresponding to the intercept of the axis of ordinate indicative of the monitor BP values MBP.

Figure 5:
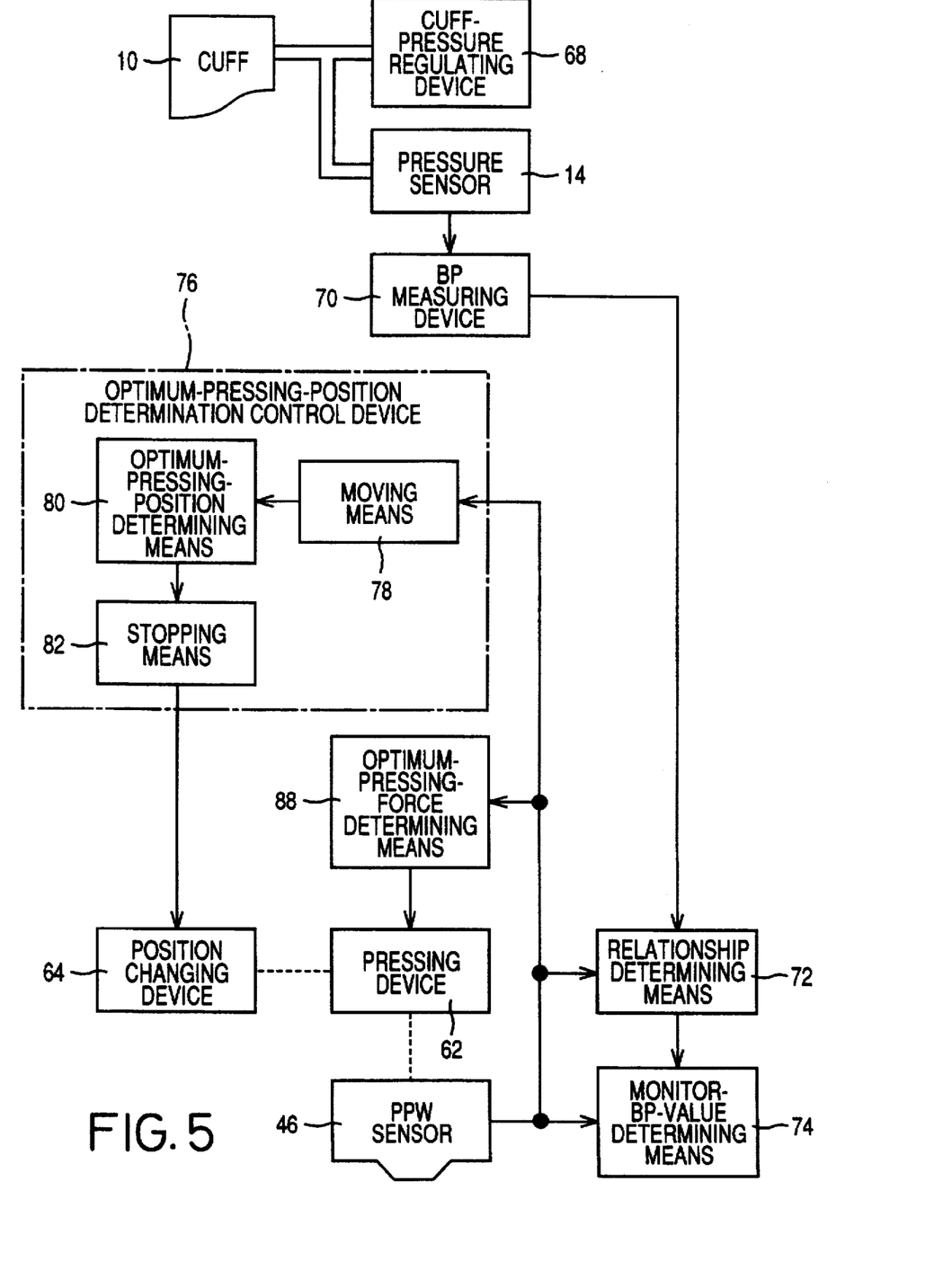
FIG. 5 is an illustrative view for explaining various functions of a control device of the BP monitor of FIG. 1.

FIG. 5 illustrates various functions of the control device 28 of the present continuous BP monitor. The selector valve 16 and the first air pump 18 cooperate with the control device 28 to provide a cuff-pressure regulating device 68 which regulates the pressure of the cuff 10 (i.e., cuff pressure), which is detected by the pressure sensor 14 when an oscillometric BP measurement using the cuff 10 is carried out. The static-pressure and pulse-wave filter circuits 24, 26 cooperate with the control device 28 to provide a BP measuring device 70 which measures, according to the oscillometric BP measuring method, a BP value of a living subject based on the variation of respective amplitudes of heartbeat-synchronous pulses of the pulse wave obtained while the pressure of the cuff 10 is slowly changed at the rate of 2 to 3 mmHg/sec. The pulse wave is represented by the pulse-wave signal $SM_1$ provided by the pulse-wave filter circuit 24. The control device 28 functions as BP-PPW relationship determining means 72 for determining a MBP-$P_M$ relationship between monitor BP values MBP and PPW magnitudes $P_M$ that is expressed by the linear function (1) and is shown in FIG. 4, based on the PPW detected by the PPW sensor 46 and the BP values BP measured by the BP measuring device 70. The control device 28 also functions as monitor-BP-value determining means 74 for successively determining, according to the MBP-$P_M$ relationship, a monitor BP value MBP of the subject based on a magnitude of each of heartbeat-synchronous pulses of the PPW detected by the PPW sensor 46.

Moreover, the control device 28 functions as a optimum-pressing-position determination control device 76 which includes moving means 78 for controlling the position changing device 64 to move the PPW sensor 46 relative to the radial artery 56 while the sensor 46 is pressed on the body surface 38 by the pressing device 62; optimum-pressing-position determining means 80 for determining an optimum pressing position of the PPW sensor 46 relative to the artery 56 based on the PPWs detected by the sensor 46 while the sensor 46 is moved by the position changing device 64 under control of the moving means 78; and stopping means 82 for controlling the position changing device 64 to stop moving the PPW sensor 46 when the optimum pressing position of the sensor 46 is determined by the optimum-pressing-position determining means 80, thereby keeping the sensor 46 at the optimum pressing position. As far as the present embodiment is concerned, the optimum pressing position of the PPW sensor 46 is defined as the position where respective pulse amplitudes of the PPWs detected by the two pressure-sensing elements respectively located at two opposite ends of the array of pressing-sensing elements provided in the press surface 54 are substantially equal to each other. The pulse amplitude of PPW is defined as the difference between the upper-peak and lower-peak magnitudes of one heartbeat-synchronous pulse of each PPW signal $SM_2$ generated by each pressure-sensing element. The moving means 78 controls the position changing device 64 to move the PPW sensor 46, when a predetermined position-changing-operation starting condition is satisfied. The position-changing-operation starting condition may be satisfied, e.g., when one of the pressure-sensing elements belonging to each of opposite end portions or ranges of the array of pressure-sensing elements of the PPW sensor 46 detects the greatest pulse amplitude of the respective pulse amplitudes detected by all the pressure-sensing elements. The PPW sensor 46 is pressed on the body surface 38 by the pressing device 62, with a predetermined first pressing force, $P_{APS1}$, or a predetermined second pressing force, $P_{APS2}$, which is greater than the first pressing force $P_{APS1}$. The moving device 78 may control the position changing device 64 such that the PPW sensor 46 is moved intermittently by each regular distance in synchronism with the heartbeat of the patient, or continuously and slowly.

Furthermore, the control device 28 functions as optimum-pressing-force determining means 88 for continuously changing the pressing force of the PPW sensor 46 applied to the body surface 38, at the optimum pressing position determined by the optimum-pressing-position determining means 76, subsequently determining an optimum pressing force $P_{HDPO}$ of the sensor 46 based on the PPWs detected by the pressure-sensing elements while the pressing force of the sensor 46 is changed, and pressing the sensor 46 on the body surface 38 with the thus determined optimum pressing force $P_{HDPO}$, according to the known control algorithm. The optimum pressing force $P_{HDPO}$ may be defined, as known in the art, as falling in a first pressing-force range whose middle value is equal to a pressing force (i.e, pressure of the chamber 48) when a certain one of the pressure-sensing elements detects a maximum heartbeat-synchronous pulse having the greatest amplitude while the pressing force of the sensor 46 is continuously changed. The certain one element may be the center one of the elements. Otherwise, the optimum pressing force $P_{HDPO}$ may be defined, as also known in the art, as falling in a second pressing-force range whose middle value corresponds to the middle point of a flat portion which is contained in a curve obtained by connecting respective lower-peak magnitudes $S_{Mmin}$ of heartbeat-synchronous pulses of the PPW signal $SM_2$ detected during the continuous changing of the pressing force of the PPW sensor 46, in a two-dimensional graph whose axis of abscissae indicates the pressing forces of the sensor 46 and whose axis of ordinate indicates the lower-peak magnitudes $S_{Mmin}$ of the signal $SM_2$. Otherwise, the optimum pressing force $P_{HDPO}$ may be defined as falling in at least one of the first and second pressing-force ranges.

Figure 6:
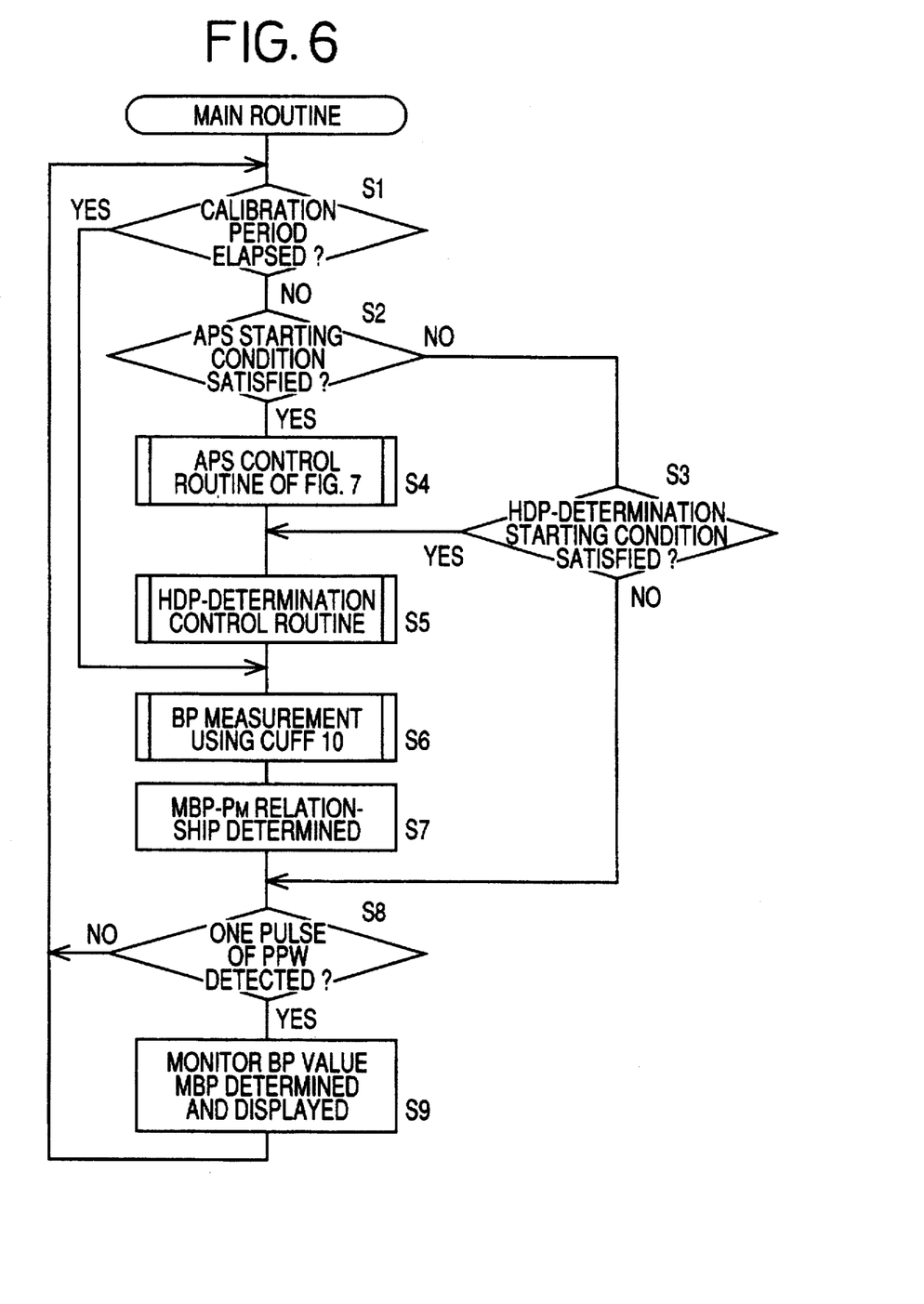
FIG. 6 is a flow chart representing a main routine which is executed by the control device of the BP monitor of FIG. 1.
Figure 7:
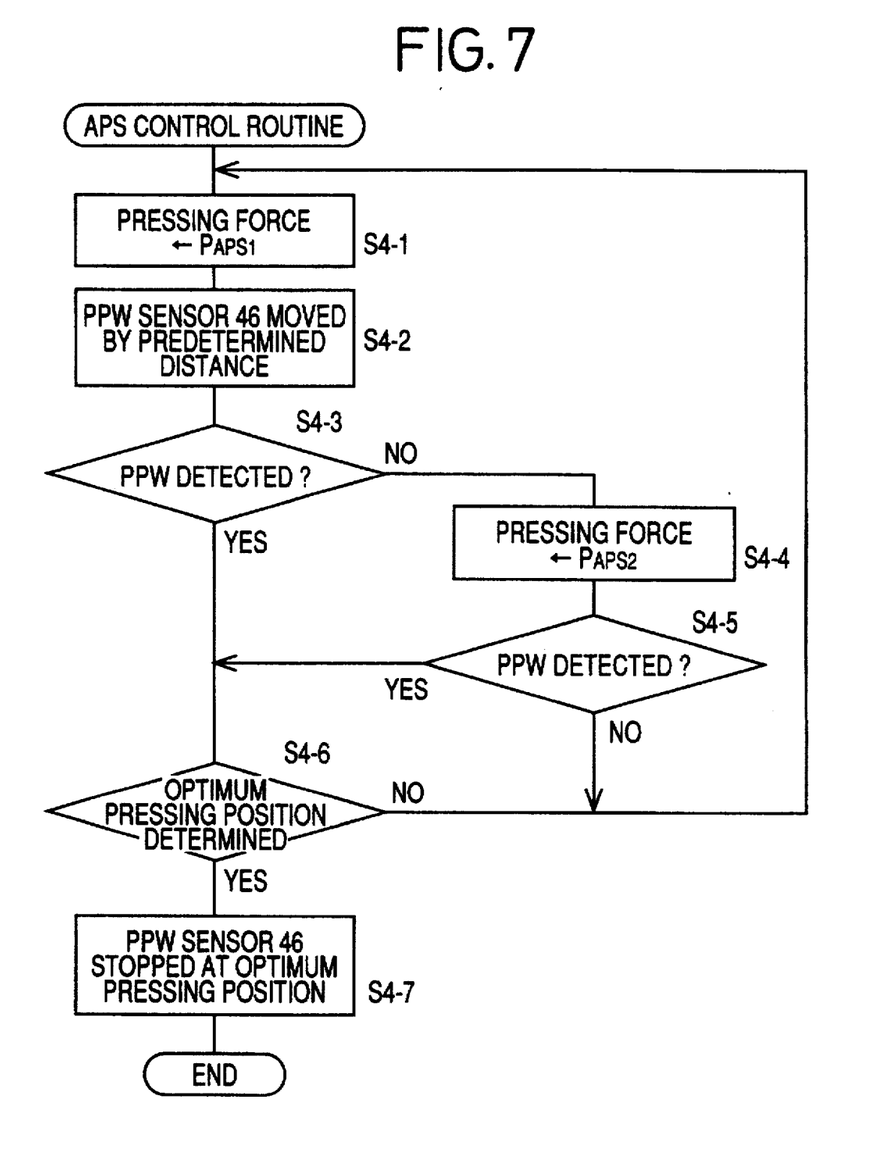
FIG. 7 is a flow chart representing an automatic-positioning-system (APS) control routine as one step of the flow chart of FIG. 6.

Hereinafter, there will be described the operation of the present continuous BP monitor constructed as described above, by reference to the flow charts of FIGS. 6 and 7. The flow chart of FIG. 6 represents a main control routine according to which the control device 28 operates, and FIG. 7 represents an automatic-positioning-system (APS) control routine as one step (or sub-routine) of the main routine of FIG. 6. According to the APS control routine, the control device 28 determines an optimum pressing position of the PPW sensor 46 relative to the radial artery 56, and stops the sensor 46 at the determined optimum pressing position.

First, at Step S1, the CPU 29 of the control device 28 judges whether a predetermined calibration period (e.g., from ten and several minutes to several tens minutes) has elapsed after a MBP-$P_M$ relationship, as shown in FIG. 4, is determined at Step S7 in the preceding control cycle in accordance with the present main routine. If a negative judgment is made at Step S1, the control of the CPU 29 proceeds with Step S2 to judge whether a predetermined position-changing-operation starting condition, i.e., APS starting condition is satisfied. The APS starting condition is satisfied when one of the pressure-sensing elements belonging to each of the two opposite end ranges of the array of pressure-sensing elements of the PPW sensor 46 detects the greatest pulse amplitude of the respective pulse amplitudes detected by all the pressure-sensing elements, as indicated at broken line in the graph of FIG. 8. Each end range of the array of pressure-sensing elements may consist of three pressure-sensing elements.

A negative judgment made at Step S2 indicates that the current position of the PPW sensor 46 relative to the radial artery 56 is not inappropriate. In this case, the control of the CPU 29 goes to Step S3 to judge whether a predetermined optimum-pressing-force determining operation starting condition, i.e., HDP (hold-down pressure) determination starting condition is satisfied. The HDP determination starting condition is satisfied when the monitor BP values MBP successively determined at Step S9 in the current control cycle have changed by more than a reference value from the BP value measured using the cuff 10 at Step S6 in the preceding control cycle. This change may result if the MBP-$P_M$ relationship determined at Step S7 in the preceding control cycle breaks, e.g., because the patient moves his or her arm on which the cuff 10 and the PPW detecting probe 34 are worn.

A negative judgment made at Step S3 indicates that the current MBP-$P_M$ relationship that was determined in the preceding control cycle has not broken. In this case, the control of the CPU 29 goes to Step S8 to judge, based on the PPW signal $SM_2$, whether one heartbeat-synchronous pulse of PPW has been detected by the PPW sensor 46. If a negative judgment is made at Step S8, the control goes back to Step S1. On the other hand, if a positive judgment is made at Step S8, the control of the CPU 29 goes to Step S9 to determine a maximum and a minimum magnitude $P_{Mmax}$, $P_{Mmin}$ of the detected one pulse represented by the PPW signal $SM_2$ supplied from the PPW sensor 46 being pressed with the optimum pressing force $P_{HDPO}$. At Step S9, the CPU 29 additionally determines a systolic and a diastolic BP value (monitor BP values) $MBP_{SYS}$, $MBP_{DIA}$ of the patient based on the determined maximum and minimum magnitude $P_{Mmax}$, $P_{Mmin}$ of the one pulse, respectively, according to the current MBP-$P_M$ relationship. The CPU 29 controls the display 32 to display the determined monitor BP values MBP together with the waveform of the one pulse of PPW detected at Step S8. Thus, the present continuous BP monitor successively determines the monitor BP values MBP for each of heartbeat-synchronous pulses of the PPW detected by the PPW sensor 46 being pressed with the optimum pressing force $P_{HDPO}$, and successively displays the determined monitor BP values MBP in digits for each pulse and continuously displays the waveform of each pulse. Step S9 corresponds to the monitor-BP-value determining means 74.

Meanwhile, if a positive judgment is made at Step S1, the control of the CPU 29 goes to Step S6 to carry out an oscillometric BP measurement using the cuff 10, and subsequently to Step S7 to update the current MBP-$P_M$ relationship by determining a new MBP-$P_M$ relationship based on the BP values measured at Step S6 and the magnitudes of the PPW newly detected by the PPW sensor 46 at Step S7. Step S7 is followed by Step S8. More specifically described, at Step S6, the CPU 29 switches the selector valve 16 to the first state thereof and operates the first air pump 18, so that the pressurized air is supplied from the pump 18 to the cuff 10 to increase the cuff pressure up to a target pressure (e.g., 180 mmHg) which is higher than an estimated systolic BP value of the patient. Subsequently, the CPU 29 stops the pump 18 and switches the valve 16 to the second state thereof, so that the cuff pressure is decreased at a low rate of 2 to 3 mmHg/sec. Based on the variation of respective amplitudes of heartbeat-synchronous pulses of the pulse wave represented by the pulse-wave signal $SM_1$ obtained during this slow decreasing of the cuff pressure, the CPU 29 determines a systolic, a mean, and a diastolic BP value $BP_{SYS}$, $BP_{MEAN}$, $BP_{DIA}$ of the patient according to a known oscillometric BP determining algorithm. In addition, the CPU 29 determines a pulse rate of the patient based on the difference between two times when successive two pulses of the pulse wave are detected, respectively. The CPU 29 controls the display 32 to display the thus measured BP values and pulse rate, and switches the valve 16 to the third state thereof to deflate quickly the cuff 10. Step S6 corresponds to the BP measuring device 70.

At Step S7, the CPU 29 determines a new MBP-$P_M$ relationship as shown in FIG. 4. More specifically described, the CPU 29 reads in one pulse of the PPW detected by the PPW sensor 46 being pressed with the optimum pressing force $P_{HDPO}$, and determines a maximum and a minimum magnitude $P_{Mmax}$, $P_{Mmin}$ of the one pulse. Based on the thus determined maximum and minimum magnitudes $P_{Mmax}$, $P_{Mmin}$ and the systolic and diastolic BP values $BP_{SYS}$, $BP_{DIA}$ measured at Step S6, the CPU 29 determines a MBP-$P_M$ relationship between monitor BP value MBP and PPW magnitude $P_M$ (i.e., magnitude or voltage of the PPW signal $SM_2$). Step S7 corresponds to the relationship determining means 72.

A positive judgment made at Step S2 indicates that the position of the PPW sensor 46 relative to the radial artery 56 has largely changed and is not appropriate any more. In this case, the control of the CPU 29 goes to Step S4, i.e., the APS control routine of FIG. 7 according to which the CPU 29 determines an optimum pressing position of the PPW sensor 46 and stops the sensor 46 at the optimum pressing position. Step S4 is followed by Step S5 to determine an optimum pressing force $P_{HDPO}$ applied to the PPW sensor 46 in the previously-described manner. When the sensor 46 is stopped or held at the optimum pressing position, the pressure-sensing elements belonging to a middle range of the array of pressure-sensing elements between the opposite end ranges thereof are positioned right above the artery 56. Thereafter, Step S6 and the following steps are carried out with the PPW sensor 46 being pressed on the body surface 38 with the optimum pressing force $P_{HDPO}$. Step S4 corresponds to the optimum-pressing-position determining means 76; and Step S5 corresponds to the optimum-pressing-force determining means 88.

If a positive judgment is made at Step S3 while monitor BP values MBP are successively determined through Steps S1, S2, S3, S8, and S9, the control of the CPU 29 goes to Step S5 and the following steps.

Hereinafter, Step S4, i.e., APS control routine will be described by reference to the flow chart of FIG. 7.

First, at Step S4-1, the CPU 29 controls the pressing device 62 to press the PPW sensor 46 with a predetermined first pressing $P_{APS1}$. Step S4-1 is followed by Step S4-2 to determine, based on the pulse amplitudes of the PPWs detected by the pressing-sensing elements provided in the press surface 54 of the sensor 46, a direction in which the sensor 46 should be moved so that the center one of the array of pressure-sensing elements may detect the greatest pulse amplitude. Subsequently, the CPU 29 controls the position changing device 64 including the feed screw 41 to move the sensor 46 by a predetermined distance in the thus determined direction while the sensor 46 is pressed with the first pressing force $P_{APS1}$. Step S4-2 corresponds to the moving means 78.

Step S4-2 is followed by Step S4-3 to judge whether one pulse of PPW has been detected by each of the pressing-sensing elements of the PPW sensor 46. If a positive judgment is made at Step S4-3, the control of the CPU 29 goes to Step S4-6 to judge whether the sensor 46 is currently located at an optimum pressing position, based on the respective PPWs detected by the pressing-sensing elements. For example, a positive judgment is made at Step S4-6 when one of the pressure-sensing elements belonging to the predetermined middle range of the array of pressure-sensing elements detects the greatest pulse amplitude, or when the two elements respectively located at the opposite two ends of the array of elements detects substantially equal pulse amplitudes. Step S4-6 corresponds to the optimum-pressing-position determining means 80.

Figure 8:
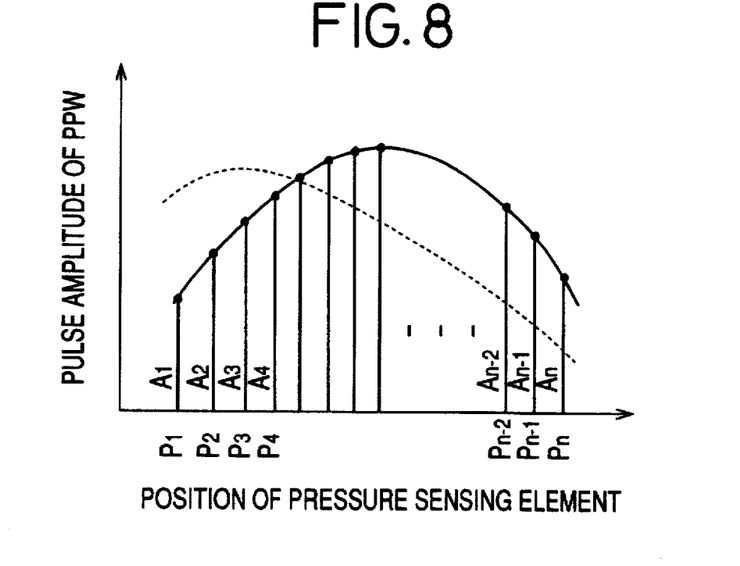
FIG. 8 is a graph showing a distribution of respective pulse amplitudes, $A_n$, of the PPWs detected by pressure-sensing elements, $P_n$, of the PPW sensor of the BP monitor of FIG. 1.

FIG. 8 shows a graph representing a distribution of respective pulse amplitudes, $A_1$ to $A_n$, of PPWs detected by the pressure-sensing elements, $P_1$ to $P_n$, provided in the press surface 54 of the PPW sensor 46. The symbol n indicates the number of the pressure-sensing elements. The axis of ordinate indicates pulse amplitude $A_n$ of PPW and the axis of abscissae indicates position of pressure-sensing element $P_n$. At Step S4-6, the CPU 29 judges whether the respective pulse amplitudes $A_1$, $A_n$ of PPWs detected by the two pressure-sensing elements $P_1$, $P_n$ located at the two opposite ends of the array of pressure-sensing elements are substantially equal to each other. In addition, one of the elements $P_n$ which detects the greatest one of the respective pulse amplitudes detected by all the elements $P_n$ is selected as an optimum pressure-sensing element that is located right above the radial artery 56, and the PPW signal $SM_2$ produced by the optimum pressure-sensing element is utilized to determine monitor BP values MBP of the patient, at Step S9 of the main routine of FIG. 6. In the graph of FIG. 8, a solid-line curve representing a distribution of respective pulse amplitudes $A_1$ to $A_n$ of the PPWs detected by the elements $P_n$ indicates that the middle range of the array of elements $P_n$ is currently located right above the artery 56, and a broken-line curve indicates that the middle range of the array of elements $P_n$ is not currently located right above the artery 56, i.e., out of position.

However, if a negative judgment is made at Step S4-3, the control of the CPU 29 goes to Step S4-4 to control the pressing device 62 to press the PPW sensor 46 with a predetermined second pressing force, $P_{APS2}$, which is greater than the first pressing force $P_{APS1}$. Step S4-4 is followed by Step S4-5 to judge, like at Step S4-3, whether one pulse of PPW has been detected by each of the elements $P_n$. If a negative judgment is made at Step S4-5, the control of the CPU 29 goes back to Step S4-1 and, at Step S4-2, the PPW sensor 46 is moved once more by the predetermined distance. While Steps S4-1 to S4-5 are repeated, a positive judgment may be made at Step S4-5. In this case, the control of the CPU 29 goes to Step S4-6 to judge whether the sensor 46 is currently located at an optimum pressing position.

If a negative judgment is made at Step S4-6, the control of the CPU 29 goes back to Step S4-1 and, at Step S4-2, the PPW sensor 46 is moved once more by the predetermined distance. While Steps S4-1 to S4-6 are repeated, a positive judgment may be made at Step S4-6. In this case, the control of the CPU 29 goes to Step S4-7 to stop moving the sensor 46 and hold the same 46 at the optimum pressing position. Thereafter, the control of the CPU 29 proceeds with Step S5 of FIG. 6, i.e., HDP determination control routine. At Step S5, the CPU 29 controls the pressing device 62 to continuously increase, starting with the first or second pressing force $PAPS_1$, $PAPS_2$, the pressing force (i.e., pressure in the pressure chamber 48) applied to the PPW sensor 46, i.e., the pressing force of the sensor 46 applied to the radial artery 56 via the body surface 38. Step S4-7 corresponds to the stopping means 82.

As is apparent from the foregoing description, in the present embodiment, the control device 28 or the optimum-pressing-position determining means 80 judges whether the PPW sensor 46 is currently located at an optimum pressing position while the sensor 46 is pressed with the first or second pressing force $P_{APS1}$, $P_{APS2}$ and is intermittently moved by each predetermined distance. This judgment is made based on the PPWs detected by the pressure-sensing elements $P_n$ of the sensor 46 while the sensor 46 is moved by the position changing device 64 under control of the moving means 78. When the optimum-pressing-position determining means 80 judges a positive judgment, the control device 28 or the stopping means 82 stops moving the sensor 46 and holds the same 46 at the optimum pressing position. Since an optimum pressing position is determined while the PPW sensor 46 is pressed and moved, an optimum pressing force $P_{HDPO}$ can be determined by continuously increasing the pressing force of the sensor 46 from the first or second pressing force $P_{APS1}$, $P_{APS2}$. In addition, since the artery 56 does not move away from below the press surface 54 of the sensor 46, an optimum pressing force $P_{HDPO}$ can be determined with reliability. Thus, it is not needed to increase, from zero, the pressing force of the sensor 46 to determine an optimum pressing force $P_{HDPO}$ after an optimum pressing position has been determined. Accordingly, an optimum pressing force $P_{HDPO}$ of the sensor 46 is quickly determined, and an interruption period in which monitor BP values MBP cannot be determined based on the PPW detected by the optimum pressure-sensing element of the sensor 46 is reduced as such. That is, the present continuous BP monitor advantageously shortens the time period in which the pressing force of the sensor 46 is continuously changed to determine an optimum pressing force $P_{HDPO}$, and shortens the interruption period in which monitor BP values MBP cannot be determined.

In addition, in the present embodiment, the PPW sensor 46 has the array of pressure-sensing elements $P_n$ in the press surface 54 in the direction in which the sensor 46 is moved by the position changing device 64, and the control device 28 or the optimum-pressing-position determining means 80 judges that the sensor 46 is currently located at an optimum pressing position, when identifying that the respective pulse amplitudes $A_1$, $A_n$ of the PPWs detected by the elements $P_1$, $P_n$ provided at the opposite ends of the array of elements $P_n$ are substantially equal to each other. Accordingly, the sensor 46 can be stopped with higher accuracy than the case where the sensor 46 is stopped when one of the elements provided in the predetermined middle range of the array of elements $P_n$ detects the greatest one of the respective pulse amplitudes detected by all the elements $P_n$.

While the present invention has been described in its preferred embodiments, the present invention may otherwise be embodied.

For example, in the illustrated embodiment, an optimum pressing position is determined at Step S4-6, when it is identified that the respective pulse amplitudes $A_1$, $A_n$ of the PPWs detected by the elements $P_1$, $P_n$ at the opposite ends of the array of elements $P_n$ are substantially equal to each other. However, an optimum pressing position may be determined when it is identified that one of the elements provided in the predetermined middle range of the array of elements $P_n$ detects the greatest one of the respective pulse amplitudes detected by all the elements $P_n$.

Although in the illustrated embodiment Steps S4-1 to S4-6 are repeated so that the PPW sensor 46 is moved by each predetermined distance in synchronism with the detection of each heartbeat-synchronous pulse of PPW, it is possible that the sensor 46 be moved continuously at a predetermined low speed. In short, according to the principle of the present invention, it is at least required that the PPW sensor 46 be moved while being pressed, for determining an optimum pressing position the PPW sensor 46.

The array of pressure-sensing elements $P_n$ provided in the press surface 54 of the PPW sensor 46 may be replaced by a single pressure-sensing element. In the latter case, an optimum pressing position may be determined when it is identified that the pulse amplitude of PPW detected by the single element becomes maximum.

While in the illustrated embodiment the BP measuring device 70 measures, according to the oscillometric BP measuring method, a BP value of a living subject based on the variation of pulse amplitudes of the pulse wave produced in the cuff 10 while the cuff pressure is changed, it is possible to modify the BP measuring device 70 to determine, according to the "Korotkoff-sound" BP measuring method, a BP value of the subject based on the appearing and disappearing of Korotkoff sounds produced from the artery 56 while the cuff pressure is changed. In the latter case, a microphone is employed to detect the appearing and disappearing of Korotkoff sounds.

Although in the illustrated embodiment the cuff 10 is worn on an upper arm 12 of a living subject and the PPW sensor 46 is worn on a wrist of the subject to detect a PPW from a radial artery of the subject, it is possible to wear the cuff 10 on a thigh of the subject and wear the sensor 46 on an ankle to detect a PPW from a dorsal pedal artery of the subject.

It is to be understood that the present invention may be embodied with other changes, improvements, and modifications that may occur to those skilled in the art without departing from the spirit and scope of the invention defined in the appended claims.

What is claimed is:

1. An apparatus for detecting a pressure pulse wave from a living subject, comprising:

a pressure pulse wave sensor which detects a pressure pulse wave which is produced from an artery of the subject;

a pressing device which presses said sensor against the artery via a body surface of the subject;

a position changing device which moves said sensor and thereby changes a position of the sensor relative to the artery in a direction of width of the artery; and a control device which determines, based on the pressure pulse wave detected by said sensor, an optimum pressing position of the sensor relative to the artery where the sensor is pressed against the artery by said pressing device, and controls said position changing device to position the sensor at said optimum pressing position, said control device comprising:

moving means for controlling said position changing device to move said sensor relative to the artery while the sensor is pressed, with a predetermined pressing force, on the body surface by said pressing device, optimum-pressing-position determining means for determining said optimum pressing position of said sensor based upon the pressure pulse wave detected by the sensor while the sensor is pressed with said predetermined pressing force on the body surface by said pressing device and is moved relative to the artery by said position changing device under control of said moving means;

stopping means for controlling said position changing device to stop moving said sensor which is being pressed with said predetermined pressing force on the body surface, when said optimum pressing position of the sensor is determined by said optimum-pressing-position determining means, and optimum-pressing-force determining means for increasing the pressing force of said pressing device from said predetermined pressing force to an increased pressing force and determining an optimum pressing force of said pressing device applied to the artery of the subject via the body surface, based on the pressure pulse wave detected by said sensor stopped at said optimum pressing position while the pressing force of said pressing device is increased from said predetermined pressing force to said increased pressing force.

2. An apparatus according to claim 1, wherein said pressure pulse wave sensor comprises a plurality of pressure-sensing elements and a press surface in which an array of said pressure sensing elements extends in a direction in which said sensor is moved by said position changing device, said press surface being adapted to be pressed against the artery via the body surface so that each of the pressure-sensing elements detects a pressure pulse wave produced from the artery.

3. An apparatus according to claim 1, wherein said optimum-pressing-position determining means comprises means for judging whether a pulse amplitude of a pressure pulse wave detected by at least one first sensing element belonging to one of opposite end ranges of said array of pressure-sensing elements is substantially equal to a pulse amplitude of a pressure pulse wave detected by at least one second sensing element belonging to the other end range of the array of pressure-sensing elements, and determining, as said optimum pressing position of said sensor, a current position of the sensor when a positive judgment is made.

4. An apparatus according to claim 3, further comprising optimum-sensing-element selecting means for selecting, as an optimum sensing element, at least one third sensing element belonging to a middle range of said array of pressure-sensing elements of said pressure pulse wave sensor stopped at said optimum pressing position, said middle range being located between said opposite end ranges.

5. An apparatus according to claim 4, further comprising a blood pressure measuring device which measures a standard blood pressure value of the subject.

6. An apparatus according to claim 5, wherein said blood pressure measuring device comprises:

an inflatable cuff which is adapted to be wound around a body portion of the subject;

a supplying device which supplies said cuff with a pressurized fluid to increase a fluid pressure in the cuff and thereby inflate the cuff;

a fluid-pressure sensor which detects the pressure of the cuff; and standard-blood-pressure determining means for determining said standard blood pressure value of the subject based on variation of pulse amplitudes of a pulse wave which is produced in said cuff and detected by said fluid-pressure sensor.

7. An apparatus according to claim 5, further comprising relations hip determining means for determining a relationship between blood pressure and pressure pulse wave magnitude, based on said standard blood pressure value measured by said blood pressure measuring device and a magnitude of the pressure pulse wave detected by said optimum sensing element of said pressure pulse wave sensor stopped at said optimum pressing position.

8. An apparatus according to claim 7, further comprising monitor-blood-pressure determining means for determining, according to said relationship determined by said relationship determining means, a monitor blood pressure value of the subject based on a magnitude of each of heartbeat-synchronous pulses of the pressure pulse wave detected by said optimum sensing element of said pressure pulse wave sensor stopped at said optimum pressing position.

9. An apparatus according to claim 8, further comprising a display device which displays at least one of said standard blood pressure value measured by said blood pressure measuring device, said monitor blood pressure value determined by said monitor-blood-pressure determining means, and a waveform of the pressure pulse wave detected by said optimum sensing element of said pressure pulse wave sensor stopped at said optimum pressing position.

10. An apparatus according to claim 1, wherein said pressing device comprises:

an elastic diaphragm to which said pressure pulse wave sensor is fixed;

a housing to which said diaphragm is fixed to cooperate with said housing to define a pressure chamber; and a supplying device which supplies said pressure chamber with a pressurized fluid to increase a fluid pressure in said pressure chamber, inflate said diaphragm, and thereby press said sensor on the body surface of the subject.

11. An apparatus according to claim 10, wherein said position changing device comprises:

an internally threaded nut which is fixed to said housing;

an externally threaded screw which is threadedly engaged with said nut; and a drive device which rotates said screw and thereby moves said pressure pulse wave sensor relative to the artery of the subject.

* * * * *